United States Patent [19]

Beach et al.

[11] Patent Number: 4,529,554
[45] Date of Patent: Jul. 16, 1985

[54] PROCESS FOR THE PREPARATION OF NICKEL YLIDES CONTAINING YLIDE LIGANDS WITH A SULFONATED GROUP V COMPONENT

[75] Inventors: David L. Beach, Gibsonia; James J. Harrison, Glenshaw, both of Pa.

[73] Assignee: Gulf Research & Development Company, Pittsburgh, Pa.

[21] Appl. No.: 179,080

[22] Filed: Aug. 18, 1980

[51] Int. Cl.³ .............................................. C07F 15/04
[52] U.S. Cl. ..................................... 556/14; 556/19; 556/20; 556/21; 556/22; 556/23; 556/30; 502/155
[58] Field of Search ................................... 260/439 R

[56] References Cited

U.S. PATENT DOCUMENTS 2,998,416  8/1961  Mendel ........................... 252/426 X
3,686,159  8/1972  Bauer et al. ..................... 252/431 X

OTHER PUBLICATIONS

The Merck Index, 9th Ed., pp. ONR-67 and ONR94 (1976).
Keim et al., "Agnew. Chem." Int. Ed., vol. 17, No. 6, pp. 467-468 (1978).

Primary Examiner—Robert V. Hines
Attorney, Agent, or Firm—Deane E. Keith; Forrest D. Stine

[57] ABSTRACT

A process is provided for preparing nickel ylides which are themselves novel compounds defined by the following Formula I:

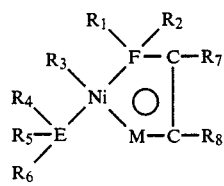

wherein $R_1$, $R_2$, $R_3$, $R_4$, $R_5$, $R_6$, $R_7$ and $R_8$ are either alike or different members selected from the group consisiting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbon atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; a hydrocarbyl group, such as defined above, carrying halogen, hydroxyl or alkoxy or aryloxy; and a sulfonato group ($-SO_3^-$) or an alkyl, aryl, alkenyl, cycloalkyl, aralkyl or alkaryl group carrying a sulfonato group; provided that at least one of $R_1$, $R_2$ and $R_3$ is a sulfonato group or an alkyl, aryl, alkenyl, cycloalkyl, aralkyl or alkaryl, as defined above, carrying a sulfonato group; M is sulfur or oxygen, preferably oxygen; E is phosphorus, arsenic, antimony or nitrogen, preferably phosphorus; and F is phosphorus, arsenic or antimony, preferably phosphorus. The process comprises reacting a ligand defined by the following formula:

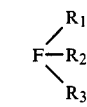

with an alpha-substituted ketone or aldehyde or an alpha-substituted thioketone or thioaldehyde defined by the following formula:

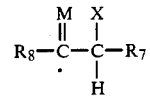

to obtain the metal salt defined by the following Formula II:

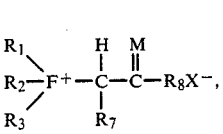

wherein $R_1$, $R_2$, $R_3$, $R_7$, $R_8$, F and M are as defined above and X is a halogen radical selected from the group consisting of fluorine, chlorine, bromine and iodine, preferably chlorine and bromine, a tosyl group (a tolune sulfonate group), or an acetate group. This metal salt is reacted with a base to obtain the novel ylide defined by the following Formula III:

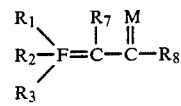

wherein $R_1$, $R_2$, $R_3$, $R_7$, $R_8$, F and M are as defined above. This ylide is then reacted with (1) a zero valent nickel compound or any nickel compound convertible to a zero valent nickel compound in situ and (2) a ligand having the formula:

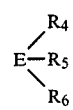

wherein $R_4$, $R_5$, $R_6$ and E are as defined above.

40 Claims, No Drawings

PROCESS FOR THE PREPARATION OF NICKEL YLIDES CONTAINING YLIDE LIGANDS WITH A SULFONATED GROUP V COMPONENT

CROSS-REFERENCES TO RELATED APPLICATIONS

Reference is made to applicant's following U.S. applications:

U.S. Patent application Ser. No. 179,079, filed Aug. 18, 1980, entitled "Nickel Ylides" and now U.S. Pat. No. 4,293,502.

U.S. Patent application Ser. No. 179,075, filed Aug. 18, 1980, entitled "Process for the Preparation of Nickel Ylides Containing Sulfonated Group V Ligands" and now abandoned.

U.S. Patent application Ser. No. 179,078, filed Aug. 18, 1980, entitled "Process for the Preparation of Nickel Ylides Containing Directly Sulfonated Ylide Ligands" and now abandoned.

U.S. Patent application Ser. No. 179,076, filed Aug. 18, 1980, entitled "Process for the Oligomerization of Ethylene" and now U.S. Pat. No. 4,293,727.

U.S. Patent application Ser. No. 179,005, filed Aug. 18, 1980, entitled "Process for the Oligomerization of Ethylene in Methanol" and now U.S. Pat. No. 4,310,716.

The disclosures of the foregoing applications are hereby incorporated by reference.

FIELD OF THE INVENTION

The present invention relates to a novel process for preparing nickel ylides which are useful as catalysts for the oligomerization of ethylene. This invention also relates to novel intermediates obtained in such a process and to the methods for preparing such intermediates.

DESCRIPTION OF THE PRIOR ART

It is well known in the art to use a variety of catalysts to oligomerize ethylene to higher molecular weight olefins. The term "oligomerize" has been employed, and is employed herein to describe the conversion of lower olefins such as ethylene to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyls or alkyl halides and titanium halides. Major disadvantages of aluminum alkyl catalysts are their highly reactive and pyrophoric nature and the fact that they must be used at relatively high temperatures, e.g., 200°–275° C. and pressures, e.g., 2000–4000 psig (13,790 to 27,580 kPa). Although much milder reaction conditions are used when the aluminum alkyls are used in conjunction with titanium halides, product quality and ease of catalyst separation from products of both of these prior art types of catalysts are not as high as desired.

An article by W. Keim, F. H. Kowaldt, R. Goddard and C. Kruger entitled "Novel Coordination of (Benzoylmethylene)triphenylphosphorane in a Nickel Oligomerization Catalyst", in *Angew. Chem. Int. Ed. Engl.* (1978) No. 6, page 466, discloses the preparation of a nickel ylide by the following reaction:

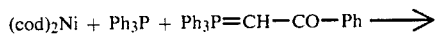

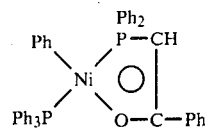

wherein "cod" represents 1,5-cyclooctadiene and "Ph" represents phenyl. It is reported that the resultant nickel ylide converts ethylene into alpha olefins or polyethylene.

SUMMARY OF THE INVENTION

A novel process has now been found for preparing nickel ylides which are themselves novel compounds defined by the following Formula I:

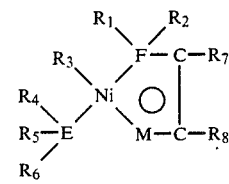

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbons atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; a hydrocarbyl group, such as defined above, carrying halogen, hydroxyl or alkoxy or aryloxy; and a sulfonato group ($—SO_3^-$) or an alkyl, aryl, alkenyl, cycloalkyl, aralkyl or alkaryl group carrying a sulfonato group; provided that at least one of $R_1$, $R_2$ and $R_3$ is a sulfonato group or an alkyl, aryl, alkenyl, cycloalkyl, aralkyl or alkaryl, as defined above, carrying a sulfonato group; M is sulfur or oxygen, preferably oxygen; E is phosphorus, arsenic, antimony or nitrogen, preferably phosphorus; and F is phosphorus, arsenic or antimony, preferably phosphorus. The process comprises reacting a ligand defined by the following formula:

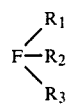

with an alpha-substituted ketone or aldehyde or an alpha-substituted thioketone or thioaldehyde defined by the following formula:

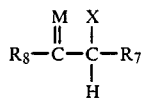

to obtain the metal salt defined by the following Formula II:

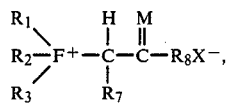

wherein $R_1$, $R_2$, $R_3$, $R_7$, $R_8$, F and M are as defined above and X is the halogen radical selected from the group consisting of fluorine, chlorine, bromine and iodine, preferably chlorine and bromine, a tosyl group (a toluene sulfonate group), or an acetate group. This metal salt is reacted with a base to obtain the novel ylide defined by the following Formula III:

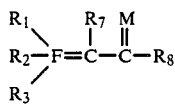

wherein $R_1$, $R_2$, $R_3$, $R_7$, $R_8$, F and M are as defined above. This ylide is then reacted with (1) a zero valent nickel compound or any nickel compound convertible to a zero valent nickel compound in situ and (2) a ligand having the formula:

$$E\begin{matrix}-R_4\\-R_5\\-R_6\end{matrix}$$

wherein $R_4$, $R_5$, $R_6$ and E are as defined above.

The presence of the sulfonato group in the nickel ylides obtained in the process of this invention induces solubility in polar solvents such as water or methanol. This facilitates product removal and separation from reaction media or the use of extractive techniques, e.g., by the use of aqueous ammonium hydroxide, not possible with the corresponding nickel ylides which do not contain a sulfonator group.

DESCRIPTION OF THE PREFERRED EMBODIMENTS

In the process of this invention, the first step involves reacting a ligand, defined by the formula:

$$F\begin{matrix}-R_1\\-R_2\\-R_3\end{matrix}$$

wherein $R_1$, $R_2$, $R_3$ and F are as defined above, with an alpha substituted ketone or aldehyde or an alpha substituted thioketone or thioaldehyde defined by the following formula:

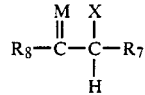

wherein $R_7$, $R_8$, M and X are as defined above. The sulfonated ligand can be obtained in any conventional manner by sulfonating the appropriate trihydrocarbyl phosphine, arsine or stibine, e.g., by sulfonating using $SO_3$ in the presence of a strong inorganic mineral acid, such as sulfuric acid, hydrochloric acid, nitric acid, phosphoric acid, etc. It is preferred to use fuming sulfuric acid ($H_2SO_4 \cdot X SO_3$, where x can be, for example, from about 0.1 to about 0.6, preferably from about 0.2 to about 0.4). The amount of $SO_3$ is not critical and can vary over a wide range, for example, at least about one mole per mole of ligand, preferably from about two to about 20 moles per mole of ligand. The two reactants are stirred and heated at a temperature of about 0° to about 200° C., preferably about 40° to about 100° C., for about one minute to about 48 hours, preferably for about 30 minutes to about four hours. Any suitable pressure can be used, although atmospheric pressure is preferred. At the end of this period the reactor contents are cooled to a temperature of about −30° to about 50° C., preferably about room temperature (about 26° C.), after which sufficient water and a suitable base, such as an alkaline metal hydroxide, an alkali metal alkoxide, ammonium hydroxide, a hydrocarbyl-substituted ammonium hydroxide, etc. are added thereto to crystallize the sulfonated ligand out of solution. For example, the amount of water used can range from about 10 milliliters to about 10 liters per mole of sulfonated ligand. The crystals can be recovered in any suitable manner, for example, by filtration, decantation or by centrifuging. Specific examples of ligands that can be used include: allyldiphenylphosphine; benzyldiphenylphosphine; bis(3-aminopropyl)phenylphosphine; bis(2-cyanoethyl)phenylphosphine; bis(m-fluorophenyl)-phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallyphenylphosphine; di-n-amylphenylphosphine; di-sec-butylphenylphosphine; dicyclohexylphenylphosphine; diethylphenylphosphine; di-n-heptylphenylphosphine; di-n-hexylphenylphosphine; dimethylphenylphosphine; dimethyl-p-tolylphosphine; diphenyl-n-butoxyphosphine; diphenylchlorophosphine; diphenylenephenylphosphine; diphenylethoxyphosphine; diphenylmethoxyphosphine; diphenylphosphine; beta-diphenylphosphinoethyltriethoxysilane; di-isopropylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomenthyldiphenylphosphine; pentafluorophenyldiphenylphosphine; (2-phenylbutyl)diphenylphosphine; phenyldi-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tris(1-naphthyl)phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphine-bis(benzene-3-sulfonate); dimethylphenylarsine; methyldiphenylarsine; triphenylarsine; tri-p-tolylarsine; diphenylchloroarsine; and triphenylantimony. Specific examples of such alpha substituted ketones or aldehydes and of alpha substituted thioketones or thioaldehydes that can be used herein include: phenacylchloride; phenacylbromide; alpha-acetoxyacetophenone; alpha-bromo-2'-acetonaphthone; alpha-bromoacetone; 3-bromocamphor; alpha-bromo-p-chloroacetophenone; alpha-bromo-2',4'-dimethoxyacetophenone; alpha-bromoiosbutyrophenone; alpha-bromo-o-methoxyacetophenone; alpha-bromo-m-methoxyacetophenone; alpha-bromo-p-methoxyacetophenone; alpha-bromo-4'-methylacetophenone; p-bromophenacrylbromide; alpha-bromopropiophenone; chloroacetone; alpha-chloro-p-fluoroacetophenone; alpha-chlorobutyrophenone; p-chlorophenacylchloride; alpha-chloropropiophenone; alpha-chlorothioacetophenone; alpha-bromothioacetophenone; alpha-chloroethylnaphthylketone; alpha-chloromethylacetate; alpha-bromomethylacetate; alpha-chloroethylacetate; alpha-bromoethylacetate; alpha-chloropropylacetate; alpha-chlorobutylacetate; alpha-chlorophenylacetate; alpha-chloro-p-sulfonatophenylacetate; alpha-bromopropylacetate; alpha-bromobutylacetate; alpha-bromophenylacetate; and alpha-bromo-p-sulfonatophenylacetate.

The reaction between the sulfonated ligand and the ketone or aldehyde is carried out using about equal molar amounts of each reactant while they are dissolved in an appropriate hydrocarbon solvent, such as toluene or tetrahydrofuran, and the reaction is carried out at a temperature of about 20° to about 200° C., preferably about 50° to about 150° C., and any suitable pressure, preferably atmospheric, for about one to about 24 hours, preferably for about two to about eight hours. The reaction mixture is then cooled, preferably to room temperature. If a solid results from such cooling it is recovered in any suitable manner, for example, by filtration, decantation or by centrifuging. If solids do not form, the reaction mixture can be subjected to distillation to remove solvents therefrom, leaving behind novel solid material, which is a salt defined by the following Formula II:

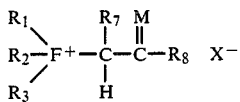

wherein $R_1$, $R_2$, $R_3$, $R_7$, $R_8$, F, M and X are as defined above.

To convert the above salt to the corresponding ylide, the salt is reacted with a stoichiometric amount of a base, such as an alkali metal hydroxide (sodium or potassium hydroxide), an alkyl or aryl lithium (n-butyl lithium, methyl lithium or phenyl lithium), an alkoxide (sodium methoxide or potassium t-butoxide), a hydrocarbylsubstituted ammonium hydroxide (benzyltrimethylammonium hydroxide), ammonium hydroxide, ammonia, etc. This can be done, for example, by suspending or dissolving the salt in a suitable liquid, such as water, an alcohol (ethanol or isopropanol), an aromatic (benzene or toluene), a hydrocarbon (hexane or heptane), etc. The reaction temperature can range from about room temperature to about 200° C., preferably from about room temperature to about 50° C., and the reaction time from about one minute to about four hours, or even longer, but preferably from about one to about two hours. Elevated pressures can be used, although atmospheric pressure will suffice. If the ylide obtained is a solid, recovery can be effected by filtration, decantation or by centrifuging. If the ylide is dissolved in the solvent, simple distillation is sufficient to remove the solvent, leaving behind the solid ylide. In some cases in association with the ylide so recovered will be the salt corresponding to the base that was used. For example, use of sodium hydroxide produces the corresponding sodium salt. The salt and the desired ylide can be separated from each other in any convenient manner, for example, by extraction with a solvent that will dissolve one and not the other. For example, aromatics, such as toluene, can be used to dissolve the ylide, while water can be used to dissolve the salt. That novel ylide obtained can be defined by the following Formula III:

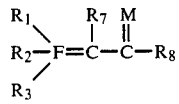

wherein $R_1$, $R_2$, $R_3$, $R_7$, $R_8$, F and M are as defined above

The above identified ylide is then reacted with (1) a ligand defined by the formula:

wherein $R_4$, $R_5$, $R_6$ and E are as defined above; and (2) a zero valent nickel compound or any nickel compound convertible to a zero valent nickel compound in situ. Specific examples of ligands that can be used include: allyldiphenylphosphine; benzyldiphenylphosphine; bis(3-aminopropyl)phenylphosphine; bis(2-cyanoethyl)-phenylphosphine; bis(m-fluorophenyl)phosphinous chloride; 4-bromophenyldiphenylphosphine; n-butyldiphenylphosphine; t-butyldiphenylphosphine; 2-cyanoethyldiphenylphosphine; cyclohexyldiphenylphosphine; n-decylphenylphosphine; diallylphenylphosphine; di-n-amylphenylphosphine; di-sec-butylphenylphosphine; dicyclohexylphenylphosphine; diethylphenylphosphine; di-n-heptylphenylphosphine; heptylphenylphosphine; di-n-hexylphenylphosphine; dimethylphenylphosphine; dimethyl-p-tolylphosphine; diphenyl-n-butoxyphosphine; diphenylchlorophosphine; diphenylenephenylphosphine; diphenylethoxyphosphine; diphenylmethoxyphosphine; diphenylphosphine; beta-diphenylphosphinoethyltriethoxysilane; di-iso-propylphenylphosphine; di-o-tolylphenylphosphine; divinylphenylphosphine; ethyldiphenylphosphine; n-hexyldiphenylphosphine; o-methoxyphenyldiphenylphosphine; (2-methylbutyl)diphenylphosphine; methyldiphenylphosphine; methylethylphenylphosphine; methylphenylphosphine; neomethyldiphenylphosphine; pentafluorophenyldiphenylphosphine; (2-phenylbutyl)diphenylphosphine; phenyldi-n-butoxyphosphine; phenyldichlorophosphine; phenyldiethoxyphosphine; phenyldimethoxyphosphine; phenylphosphine; isopropyldiphenylphosphine; n-propyldiphenylphosphine; o-tolyldiphenylphosphine; p-tolyldiphenylphosphine; tribenzylphosphine; tris(m-chlorophenyl)phosphine; tris(p-chlorophenyl)phosphine; tri(l-naphthyl)phosphine; triphenylphosphine; tris(4-dimethylaminophenyl)phosphine; tris(p-fluorophenyl)phosphine; tris(o-methoxyphenyl)phosphine; tris(p-methoxyphenyl)phosphine; tri-o-tolylphosphine; tri-m-tolylphosphine; tri-p-tolylphosphine; vinyldiphenylphosphine; sodium diphenylphosphinebenzene-3-sulfonate; disodium phenylphosphine-bis(benzene-3-sulfonate); dimethylphenylarsine; methyldiphenylarsine; triphenylarsine; tri-p-tolylarsine; diphenylchloroarsine; triphenylantimony; triphenylamine; tribenzylamine; methyldiphenylamine; dimethylphenylamine; bis(2-cyanoethyl)phosphine; bis(dimethylamino)methylphosphine; t-butyldichlorophosphine; 2-cyanoethylphosphine; cyclohexylphosphine; di-t-butylchlorophosphine; dicyclohexylphosphine; diethylethoxyphosphine; diethyl-iso-propoxyphosphine; diethylphosphine; triallylphosphine; tri-isobutylphosphine; tri-n-butylphosphine; tri-sec-butylphosphine; tri-t-butylphosphine; triethylphosphine; tri-n-hexylphosphine; trimethylphosphine; trifluorophosphine; tri-iso-propylphosphine; tri-n-propylphosphine; tris(2-cyanoethyl)phosphine; tris(dimethylamino)phosphine; tris-(trimethylsilyl)phosphine; tri-n-butylantimony; triethylarsine; trimethylarsine; methyldiiodoarsine; trimethylamine; triethylamine; tributylamine; tripropylamine; dimethylamine; di-n-hexylamine; dicyclohexylamine; diethylamine; tricyclohexylamine; ammonia; and phosphine. Specific examples of zero valent nickel compounds or nickel compounds convertible to a zero valent nickel compound in situ which can be used include: tris(triphenylphosphine)nickel; bis(cyclooctadiene)nickel; tetrakis(triphenylphosphine)nickel; bis(-norbornadiene)nickel; (cycloocta-1,5-diene)duroquinone nickel; (dicyclopentadiene)duroquinone nickel; bis(tetracyclone)nickel; tetrakis(triethylphosphine)nickel; tris-(triethylphosphine)nickel; bis(triphenylphosphine)nickel dicarbonyl; nickel carbonyl; nickel(II)acetylacetonate; nickelocene; bis(triethylphosphine)nickel(II)chloride; tetrakis(trifluorophosphine)nickel; nickel acetate; nickel bromide; nickel carbonate; nickel chloride; nickel fluoride; nickel iodide; nickel nitrate; nickel sulfate; nickel 2,4-pentanedionate; bis$\pi$-allyl nickel; and nickel dichloride hexaamine.

In this step, approximately equal molar amounts of each of the three reactants defined above are dissolved in any suitable unreactive solvent, such as toluene, tetrahydrofuran, dioxane, or other unreactive hydrocarbon solvents, and stirred while maintaining a temperature of about 0° to about 100° C., preferably room temperature, for about one-half hour to about 48 hours, preferably about three to about 20 hours, sufficient to ensure complete reaction. Any suitable pressure can be used, although atmospheric pressure is preferred. The solvent can be removed from the reaction mixture in any suitable manner, for example, by distillation, including vacuum distillation, if necessary, leaving behind the novel compound defined above. On the other hand, a second solvent in which the desired product is insoluble, such as heptane, can be added to the reaction product to precipitate the novel compound therein. Then novel compound can be recovered, for example, by filtration, decantation or by centrifuging.

Specific examples of nickel ylides which can be prepared by the practice of this invention are set forth in Table I. In this table and as used elsewhere herein, "Ph" represents phenyl.

TABLE I

| Compound | $R_1$ | $R_2$ | $R_3$ | $R_4$ | $R_5$ | $R_6$ | $R_7$ | $R_8$ | E | F | M |
|---|---|---|---|---|---|---|---|---|---|---|---|
| 1 | Ph | Ph | –C$_6$H$_4$–SO$_3^-$ | Ph | Ph | Ph | H | Ph | P | P | O |
| 2 | –C$_6$H$_4$–SO$_3^-$ | Ph | Ph | Ph | Ph | Ph | H | Ph | P | P | O |
| 3 | –C$_6$H$_4$–SO$_3^-$ | Ph | Ph | Ph | –C$_6$H$_4$–SO$_3^-$ | Ph | H | Ph | P | P | O |
| 4 | Ph | –C$_6$H$_4$–SO$_3^-$ | Ph | Ph | Ph | Ph | H | OCH$_3$ | P | P | O |
| 5 | Ph | CH$_3$ | –C$_6$H$_4$–SO$_3^-$ | Ph | Ph | Ph | H | OC$_4$H$_9$ | P | P | S |
| 6 | Ph | –C$_6$H$_4$–SO$_3^-$ | Ph | Ph | Ph | Ph | SO$_3^-$ | O–C$_6$H$_4$–SO$_3^-$ | P | P | O |
| 7 | Ph | –C$_6$H$_4$–SO$_3^-$ | Ph | Ph | Ph | Ph | H | CH$_3$ | P | As | O |
| 8 | Ph | –C$_6$H$_4$–SO$_3^-$ | Ph | Ph | Ph | Ph | H | –C$_6$H$_4$–OCH$_3$ | P | P | O |

The following examples illustrate the invention, and are not intended to limit the invention, but rather, are presented for purposes of illustration. Example I illustrates the preparation of a nickel ylide in accordance with the practice of this invention; and Example II illustrates the use of this nickel ylide to oligomerize ethylene.

EXAMPLE I

To 4.65 grams of alpha-chloroacetophenone (0.03 mole) in 150 milliliters of toluene there were added 10.92 grams of sodium diphenylphosphinobenzene-3-sulfonate (0.03 mole). This was heated to reflux under argon for five hours and then cooled and filtered. A total of 14.52 grams of the novel phosphonium salt:

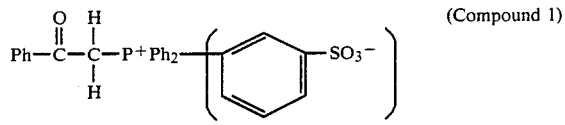
(Compound 1)

was obtained which was suspended in ethanol/water and titrated with 10 percent sodium hydroxide to a phenolphthalein end point. The ethanol was removed in vacuo and the product was washed with toluene to remove a small amount of unsubstituted benzoylmethylene triphenylphosphorane (1.2 grams). A total of 12.89 grams of the following novel phosphonium compound:

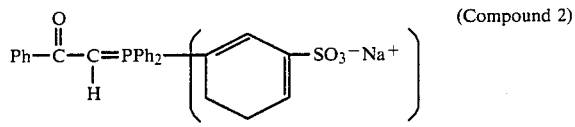
(Compound 2)

was obtained in 89 percent yield.

To 1.38 grams of bis(cyclooctadiene)nickel (five millimoles) in 70 milliliters of tetrahydrofuran there was added a mixture of 1.31 grams of triphenylphosphine (five millimoles) and 2.41 grams of Compound 2 (five millimoles) dissolved in 70 milliliters of tetrahydrofuran. This was stirred at room temperature for 18 hours, after which the solvent was removed in vacuo. The resulting product was dissolved in toluene and filtered. Heptane was then added to precipitate the following novel nickel ylide;

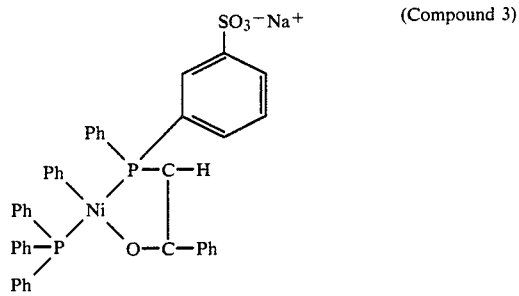
(Compound 3)

EXAMPLE II

A run was carried out wherein there was charged 0.1 millimole of the sulfonated nickel ylide catalyst obtained in Example I, Compound 3, dissolved in 100 milliliters of toluene. During the reaction precautions were taken to exclude air contamination by performing the reaction in an argon atmosphere. The reaction mixture was then heated to 50° C. and pressure with ethylene to obtain a partial pressure thereof of 200 pounds per square inch gauge (1400 kPa). The reaction mixture was stirred throughout the reaction period of two hours, during which time the temperature and pressure were maintained constant. At the end of the two-hour period the reaction mixture was cooled to room temperature and unreacted ethylene removed therefrom by distillation. The amount of oligomer produced was determined and compared with the activity for the compound reported by the Keim et al article previously discussed. The results obtained are set forth in Table II.

TABLE II

| Run No. | Nickel Ylide Catalyst | Activity: Moles Ethylene Converted Per Mole of Nickel Catalyst |
|---|---|---|
| I | Keim et al specific catalyst | 6,000* |
| II | Compound 3 | 6,965 |

*Reported by Keim et al compound 3 is more active than the unsulfonated nickel ylide of Keim et al. An additional advantage of Compound 3 over that of Keim et al lies in its easy recovery from the reaction product.

Although the invention has been described in considerable detail with particular reference to certain preferred embodiments thereof, variations and modifications can be effected within the spirit and scope of the invention as described hereinbefore, and as defined in the appended claims.

We claim:

1. A process for preparing a nickel ylide which comprises reacting a sulfonated ligand defined by the following formula:

with an alpha-substituted ketone or aldehyde or an alphasubstituted thioketone or thioaldehyde defined by the following formula:

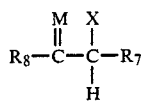

to obtain the metal salt defined by the following formula:

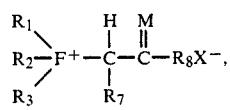

reacting the metal salt so obtained with a base to obtain the following metal ylide:

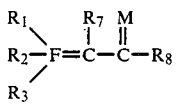

and then reacting the metal ylide with (1) a ligand defined by the following formula:

and (2) a zero valent nickel compound or any nickel compound convertible to a zero valent nickel compound in situ, wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, aryl radicals having from about six to about 20 carbon atoms, alkenyl radicals having from about two to about 30 carbon atoms, cycloalkyl radicals having from about three to about 40 carbon atoms, aralkyl and alkaryl radicals having from about six to about 40 carbon atoms, halogen radicals, hydroxyl, alkoxy or aryloxy groups, hydrocarbyl groups carrying halogen, hydroxyl, alkoxy or aryloxy, and a sulfonato group or an alkyl, aryl, alkenyl, cycloalkyl aralkyl or alkaryl group carrying a sulfonato group, provided that at least one of $R_1$, $R_2$ and $R_3$ is a sulfonato group or an alkyl, aryl, alkenyl, cycloalkyl, alkaryl or aralkyl carrying a sulfonato group; M is sulfur or oxygen; E is phosphorus, arsenic, antimony or nitrogen; F is phosphorus, arsenic or antimony; and X is a halogen radical, a tosyl group or an acetate group.

2. A process as defined in claim 1 wherein E and F are both phosphorus and M is oxygen.

3. A process as defined in claim 1 wherein each of $R_1$, $R_2$ and $R_3$ is phenyl, one of which is substituted with a sulfonato group.

4. A process as defined in claim 2 wherein each of $R_1$, $R_2$ and $R_3$ is phenyl, one of which is substituted with a sulfonato group.

5. A process as defined in claim 1 wherein each of $R_4$, $R_5$, $R_6$ and $R_8$ is phenyl and $R_7$ is hydrogen.

6. A process as defined in claim 2 wherein each of $R_4$, $R_5$, $R_6$ and $R_8$ is phenyl and $R_7$ is hydrogen.

7. A process as defined in claim 3 wherein each of $R_4$, $R_5$, $R_6$ and $R_8$ is phenyl and $R_7$ is hydrogen.

8. A process as defined in claim 4 wherein each of $R_4$, $R_5$, $R_6$ and $R_8$ is phenyl and $R_7$ is hydrogen.

9. A process as defined in claim 1 wherein the reaction between the sulfonated ligand and the ketone or aldehyde is carried out at a temperature of about 20° to about 200° C. for about one to about 24 hours.

10. A process as defined in claim 1 wherein the reaction between the sulfonated ligand and the ketone or aldehyde is carried out at a temperature of about 50° to about 150° C. for about two to about eight hours.

11. A process as defined in claim 8 wherein the reaction between the sulfonated ligand and the ketone or aldehyde is carried out at a temperature of about 20° to about 200° C. for about one to about 24 hours.

12. A process as defined in claim 8 wherein the reaction between the sulfonated ligand and the ketone or aldehyde is carried out at a temperature of about 50° to about 150° C. for about two to about eight hours.

13. A process as defined in claim 1 wherein said metal salt is converted to the corresponding ylide by reacting with a base at a temperature of from about room temperature to about 200° C. for about one minute to about four hours.

14. A process as defined in claim 1 wherein said metal salt is converted to the corresponding ylide by reacting with a base at a temperature of from about room temperature to about 50° C. for about one to about two hours.

15. A process as defined in claim 8 wherein said metal salt is converted to the corresponding ylide by reacting with a base at a temperature of from about room temperature to about 200° C. for about one minute to about four hours.

16. A process as defined in claim 8 wherein said metal salt is converted to the corresponding ylide by reacting with a base at a temperature of from about room temperature to about 50° C. for about one to about two hours.

17. A process as defined in claim 9 wherein said metal salt is converted to the corresponding ylide by reacting with a base at a temperature of from about room temperature to about 200° C. for about one minute to about four hours.

18. A process as defined in claim 12 wherein said metal salt is converted to the corresponding ylide by reacting with a base at a temperature of from about room temperature to about 50° C. for about one to about two hours.

19. A process as defined in claim 1 wherein the ligand, the zero valent nickel compound and the ylide are reacted at a temperature of about 0° to about 100° C. for about one-half to about 48 hours.

20. A process as defined in claim 1 wherein the ligand, the zero valent nickel compound and the ylide are reacted at about room temperature for about three to about 20 hours.

21. A process as defined in claim 8 wherein the ligand, the zero valent nickel compound and the ylide are reacted at a temperature of about 0° to about 100° C. for about one-half to about 48 hours.

22. A process as defined in claim 8 wherein the ligand, the zero valent nickel compound and the ylide are reacted at about room temperature for about three to about 20 hours.

23. A process as defined in claim 17 wherein the ligand, the zero valent nickel compound and the ylide are reacted at a temperature of about 0° to about 100° C. for about one-half to about 48 hours.

24. A process as defined in claim 18 wherein the ligand, the zero valent nickel compound and the ylide are reacted to about room temperature for about three to about 20 hours.

25. A process as defined in claim 1 wherein said zero valent nickel compound is bis(cyclooctadiene) nickel.

26. A process as defined in claim 8 wherein said zero valent nickel compound is bis(cyclooctadiene) nickel.

27. A process as defined in claim 9 wherein said zero valent nickel compound is bis(cyclooctadiene) nickel.

28. A process as defined in claim 12 wherein said zero valent nickel compound is bis(cyclooctadiene) nickel.

29. A process as defined in claim 13 wherein said zero valent nickel compound is bis(cyclooctadiene) nickel.

30. A process as defined in claim 16 wherein said zero valent nickel compound is bis(cyclooctadiene) nickel.

31. A process as defined in claim 17 wherein said zero valent nickel compound is bis(cyclooctadiene) nickel.

32. A process as defined in claim 18 wherein said zero valent nickel compound is bis(cyclooctadiene) nickel.

33. A process as defined in claim 19 wherein said zero valent nickel compound is bis(cyclooctadiene) nickel.

34. A process as defined in claim 22 wherein said zero valent nickel compound is bis(cyclooctadiene) nickel.

35. A process as defined in claim 23 wherein said zero valent nickel compound is bis(cyclooctadiene) nickel.

36. A process as defined in claim 24 wherein said zero valent nickel compound is bis(cyclooctadiene) nickel.

37. A process as defined in claim 26 wherein X is chlorine.

38. A process as defined in claim 28 wherein X is chlorine.

39. A process as defined in claim 32 wherein X is chlorine.

40. A process as defined in claim 36 wherein X is chlorine.

* * * * *

UNITED STATES PATENT AND TRADEMARK OFFICE
CERTIFICATE OF CORRECTION

PATENT NO. : 4,529,554

DATED : July 16, 1985

INVENTOR(S) : David L. Beach, et al.

It is certified that error appears in the above-identified patent and that said Letters Patent are hereby corrected as shown below:

Column 6, lines 54-55 thereof, delete "heptylphenylphosphine;"

Signed and Sealed this

Twenty-ninth Day of April 1986

[SEAL]

Attest:

DONALD J. QUIGG

Attesting Officer

Commissioner of Patents and Trademarks